United States Patent
Crosby

(10) Patent No.: US 9,566,184 B2
(45) Date of Patent: Feb. 14, 2017

(54) ERECTION SIMULATOR PROSTHSESIS

(71) Applicant: Ricky Lynn Crosby, Boiling Springs, SC (US)

(72) Inventor: Ricky Lynn Crosby, Boiling Springs, SC (US)

(*) Notice: Subject to any disclaimer, the term of this patent is extended or adjusted under 35 U.S.C. 154(b) by 33 days.

(21) Appl. No.: 14/251,902

(22) Filed: Apr. 14, 2014

(65) Prior Publication Data

US 2015/0290022 A1    Oct. 15, 2015

(51) Int. Cl.
*A61F 5/00* (2006.01)
*A61F 5/41* (2006.01)

(52) U.S. Cl.
CPC ............ *A61F 5/41* (2013.01); *A61F 2005/411* (2013.01)

(58) Field of Classification Search
CPC .............................. A61F 5/41; A61F 2005/411
USPC ....................................................... 600/38–41
See application file for complete search history.

(56) References Cited

U.S. PATENT DOCUMENTS

| | | | | |
|---|---|---|---|---|
| 2,899,957 A * | 8/1959 | Briggs | ...................... | A61F 5/41 600/39 |
| 4,602,625 A * | 7/1986 | Yachia | ...................... | A61F 2/26 600/40 |
| 4,893,616 A * | 1/1990 | Immonen | .................. | A61F 5/41 600/39 |
| 5,360,390 A * | 11/1994 | Maanum | ................... | A61F 5/41 600/39 |
| 5,535,758 A * | 7/1996 | Hagihara | .................. | A61F 5/41 128/897 |
| 2006/0063971 A1* | 3/2006 | Hill | ........................... | A61F 5/41 600/38 |
| 2010/0204542 A1* | 8/2010 | Hodge | ...................... | A61F 5/41 600/39 |
| 2013/0296645 A1* | 11/2013 | Evans | ..................... | A61H 19/50 600/41 |

* cited by examiner

*Primary Examiner* — John Lacyk

(57) ABSTRACT

This is a device that is provided or used as prosthesis in supporting the penis of a wearer, during intercourse. One embodiment is of a prosthesis is to aid the ability for a fully or partially impotent man to be able to perform sexual intercourse. Another embodiment of the prosthesis is that it will be able to mount on a penis that is partially erect. One embodiment of the prosthesis is of a type having a rigid body that is tubular in shape that the non erect or partially erect penis is mounted onto the penis in order to simulate a physical male erection (11) which is constructed with a slot (12) to mount the prosthesis during sexual intercourse and it holds the bottom of the penis in place and exposed while and during the act of intercourse. This exposes the sensitive area of the penis (which is behind the head of the penis) is exposed and allows for pleasure and orgasm. The cone (10) allows the insertion of the prosthesis into the sex canal of the partner without discomfort. The material (13) is constructed of a rigid penis like tubular construction in order to simulate a physical erection of a male. It is attached to the penis by a special tape that adheres to the prosthesis but does not adhere to the sensitive area of the penis and will not cause painful removal from the skin. Any adhesive tape is acceptable. Other embodiments are described and shown.

6 Claims, 3 Drawing Sheets

Bottom View

Bottom View

ERECTION SIMULATOR PROSTHSESIS

BACKGROUND

For a variety of reasons some men are totally or partially affected by impotence. Impotence is where a man is unable to achieve a penile erection. These causes or factors have been associated with blood flow to the penis and are widely studied and are under continued examination. These causes are due to a wide variety of factors, including both physical (medical) and mental (psychological) reasons. Due to the status of health of men today who suffer from diabetes, high blood pressure and other problems, there is a tendency for men to suffer from impotence. Impotence is the inability for some men to be able to have a natural penile erection. Millions of men suffer from this condition. To help solve this condition men resort to taking pills such as Cialis, or Viagra in order to achieve a physical erection. The problem is that only a many men can not achieve an erection using these drugs or are healthy enough to use these drugs. The vast majority of men cannot afford the large expense associated with purchasing these very expensive pills. There is a need for something simple and cost effective that will fit on a wide variety of different sizes of male penises so they can perform intercourse even while suffering with impotence. Even though a man suffers with impotency, this does not mean that he does not feel sensation in his penis or have the ability to achieve orgasm. Even suffering from impotence, the man can still have the feelings and sensations associated with sexual intercourse.

In many cases the causes associated with impotence may leave the male either partially or fully impotent. The results cause the male to achieve a partial erection but unable to achieve enough stiffness to be able to have intercourse. Sometimes the penis is unable for the vessels to be engorged at all leaving the penis in a limp state continually. During intercourse the sexual partner is left unsatisfied and the male is unable to keep the penis erect or achieve satisfaction. A wide variety of products, have been developed to help assist the impotent male to maintain an erection, both chemical and physical. Some have committed to surgical implants, which when finished can simulate a penis to become erect. Some have external aids that when applied or installed serve to simulate a penis to become erect. In this case we are considering the external type of aid to the impotent man. This relates to the prosthesis that is described herein and applies to the impotent man.

PRIOR ART

The following is a tabulation of some prior art that presently appears relevant.

| U.S. Patents | | | |
|---|---|---|---|
| Pat. No. | Kind Code | Issue Date | Patentee |
| 2,899,957 | | August 1959 | Briggs |
| 3,495,588 | | February 1970 | Walters |
| 3,648,700 | | March 1972 | Warner |
| 3,920,007 | | November 1975 | Line |
| 3,939,827 | | February 1976 | Brunsletter |
| 3,982,530 | | September 1976 | Storch |
| 4,074,712 | | February 1978 | Wright |
| 4,194,502 | | 311980 | Eckels |
| 4,224,933 | | September 1980 | Reiling |
| 4,449,521 | | May 1984 | Panzer |
| 4,615,337 | | October 1986 | Allinson |
| 4,672,954 | | June 1987 | Panzer |
| 4,893,616 | | January 1990 | Immonen |
| 4,972,849 | | II/1990 | Park |
| 5,360,390 | | II/1994 | Maanum. |
| 5,911,686 | | June 1999 | Kohut |
| 6,186,943 | B1 | Feb. 13, 2001 | Pan |

| U. S. patent application Publication | | | |
|---|---|---|---|
| Publication Nr. | Kind Code | Publ. Date | Applicant |

| Foreign Patent Documents | | | | |
|---|---|---|---|---|
| Foreign Doc. Nr. | Cntry Code | Kind Code | Pub Dt. | App or Patentee |
| 2221116 | | | October 1974 | France |

Because of the increase of high blood pressure and diabetes or by other health problems, there is a great increase in the occurrence of impotence in men today. This has caused the increase of the tendency for men to either have a reduced ability to have a complete penile erection because the blood does not completely engorge the penis or does not engorge the penis at all. This tendency has facilitated the requirement for either chemical treatment or by physical means by prosthesis. Because of the increase of cost in chemical treatment this would predicate a less expensive and physical prostheses instead of chemical treatment. Within this examination, we will look at these physical methods.

In U.S. Pat. No. 5,360,390 efforts were made in construction to facilitate the use of a physical prosthesis in order to achieve the ability to perform intercourse. This device seems to assume that every penis is the same length and width. There is a trough built into the device in order to account for a seemingly varied sizes and widths but it is a rigid device that is limited due to construction. There is a wraparound of latex to secure the penis. Because of the bulky nature of the device, the use of prophylactic condom will be required in order to facilitate the usage. The bulky nature of the device would be uncomfortable for the partner that the device is being inserted into. Because of the trough there could be a pinching of the penis that would be uncomfortable to the wearer. Because penises vary in length if the wearer is longer than the device there would be a bending of the penis to make intercourse painful. If it were too short the gland that is behind the head of the penis, where the sensation occurs during intercourse, would be unexposed with no sensation to the wearer.

In the U.S. Pat. No. 5,360,390 the term "substantial longitudinal flexibility" and variants there of refer to that flexibility, that is flexibility sufficient for the comfort and allow for the fluctuation in the penile engorgement, while at the same time sufficiently rigid to simulate an partial erection while in use. The frame is made up of slats covered by latex material.

In the U.S. Pat. No. 5,360,390 the design for men who are uncircumcised is not accounted for. When the foreskin is rolled back in order to have intercourse the prosthesis will pinch the foreskin and cause discomfort to the wearer.

In U.S. Pat. No. 5,911,686 it is constructed by using coated bent wires to fit around the penis with the attaching by rubber bands around the penis and around the scrotum. The forks on the end are made to fit around the head of the penis. This configuration assumes that every penis is the same length and width. A man with a penis that is longer than the construction length would cause the penis hang over and cause discomfort for the wearer. For a man that has a shorter penis than the construction length it would not fit into the prosthesis. A prophylactic condom would have to fit around the penis and the device in order to the different widths.

In U.S. Pat. No. 5,911,686 being constructed by using coated bent wires, even if they are polymer in construction, could cause a poking or pinching in the partner that it is inserted into. By having a dull flat end on the front part of the device that is close to the forks that holds the head of the penis, could cause a poking or jabbing in the partner when it is inserted into the partner by the wearer, there is the strong possibility of injury to the partner.

In U.S. Pat. No. 6,186,943 the construction is made up of a flat washer and tube to make it rigid and the attaching method is by strings. The unique design is simple and direct. It is made of two pieces: (1) with the flat washer and stem and (2) with the string in a small tube with the string inserted. The tube is inserted into the stem and forms the length. This method requires that the penis be the same length. If the penis is too long for the device then there is the possibility of bending the penis which will cause discomfort and pain. If the penis is too short the string may fit but there is the strong possibility of the poking the partner by means of the tube. It the tube is too weak then the penis would not be able to perform intercourse. If the tube were too strong then the sticking and poking of the inside of the partner is very strong. Over time the strings weakening would cause difficulty. Because of the nature of the tube being filled with string, to make it sanitary, the string would have to be removed and cleaned each time intercourse were performed. The lack of cleaning could result in infection and disease.

In U.S. Pat. No. 5,667,471 it is constructed by a notched cone shaped cylinder that fits around the penis with a locking strap that goes around the male's scrotum. This is a simple device that does not account for the different lengths of the male penis. If the penis is too long it will cause the penis to bend causing discomfort and pain. It the penis is too short the sensitive gland below the head of the penis that causes sensation is not exposed for the pleasure that intercourse is intended. This does not account for men that are not circumcised.

There is one aspect to this invention that is described as prosthesis. This is to be provided as a support for a penis that is partially or fully impotent during intercourse. This prosthesis is comprised of a rigid material with a slot in a solid, unitized construction, without seams, sized for a penis to be inserted into the tubular body and located closest to the body at the base of the penis.

The penile slot runs approximately ⅔rds of the length of the prosthesis with the closed end being cone shaped, for easy penetration, and the other end open for the insertion of the penis. The penile slot is intended to be used in the down position so as to expose the penile gland to the action of intercourse. The attaching method will be varied but preferred is the use of a special tape with adhesive to attach to the prosthesis and non adhesive wrapped around the penis and scrotum. This will leave the sensitive gland of the penis to ride in the penile slot so as to expose the penis to the full pleasure of intercourse and achieve an orgasm. For men who are healthy enough to have sexual intercourse, they can still have a sexual experience resulting in an orgasm. The Erection Simulator Prosthesis will allow an impotent man to insert his non erect penis into the prosthesis and have what is normal sexual intercourse as though his penis were erect. This allows him to please his mate and achieve and orgasm.

ADVANTAGES

Accordingly several advantages of one or more aspects are as follows: to provide a cheap and practical way for a man who suffers with impotence (the inability to achieve a physical penile erection), to be able to perform sexual intercourse. This fills the need that other prosthesis' are not able to provide. It allows a man to fit the prosthesis onto his penis without regard to the length or width of his penis. If a man is able to achieve a partial erection or no erection at all, it is designed to fit both needs. One big advantage is that the prosthesis gives allowance for men that are uncircumcised. Before intercourse, an uncircumcised male can just roll the foreskin back on his penis before inserting his penis into the penile slot of the prosthesis. Because there is plenty of room inside, and the prosthesis will hold the foreskin back, and hold the penis in place, there is a comfortable fit. This will allow a comfortable fit for a variety of sizes of male penises. When intercourse is finished, the prosthesis can be removed, cleaned, and sanitized to prevent infection or disease. The cleaning is simple and can be performed without special products or solutions. The prosthesis can be attached firmly to the penis without elaborate and expensive methods which other products require. This is also an advantage that other devises do not provide. The prosthesis has no sharp or blunt edges to incur injury or discomfort to the partner or to the wearer. The prosthesis is formed as a unitized construction that is made of one piece of ridged material or of a combination of materials to accomplish its purpose. It has no places for bacteria to hide and be able to infect the partner. The prosthesis is made with a penile slot in order for a penis to be inserted into easily. It is wide enough to fit and hold the penis in place during intercourse. The end that is to be inserted into the partner is of a cone (does not have to only be of a cone shape) design for ease insertion and comfort to the partner. There are no elaborate tie downs needed in the construction, these are unreliable and may cause discomfort. This is a real advantage over other prosthesis'. The attaching system is simple; it is special adhesive tape that is long enough to wrap around the prosthesis and the penis at the base of the penis and scrotum. The special tape is constructed in such a way that it does not adhere to the fleshy part of the penis to make it pull and become painful to the man when removed. This special tape is cheap and very sturdy to perform intercourse even if the penis is very limp, and the tape on the prosthesis can be removed easily and painlessly. Any adhesive tape is acceptable though. It is a design that requires no special and in depth instructions to operate. Other advantages of one or more aspects will be apparent from consideration of the drawings and ensuing description.

SUMMARY

In accordance with one embodiment the Erection Simulator Prosthesis is used to mount onto a penis that is impotent (unable to achieve a physical erection or full erection). At this point a special tape (that has adhesive to attach to the prosthesis and will not adhere to the skin) is wrapped around the penis/scrotum at the base of the prosthesis and the penis closest to the body. Any adhesive tape is acceptable though. Holding the prosthesis in place, the man is able to insert the penis mounted prosthesis into the sexual canal and perform sexual intercourse with full sensation. It will allow the man to have the full performance of sexual intercourse as though he were able to have his penis in the full erect position.

BRIEF DESCRIPTION

In the drawings, there are different figures that are closely related but having different numbers.

DRAWING

Figure 1A:
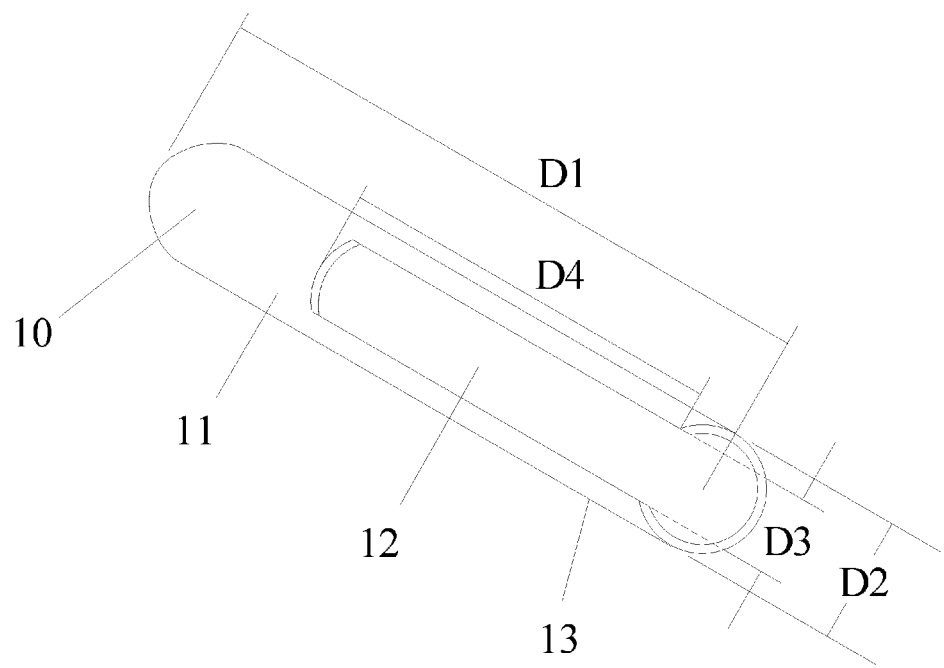
FIG. 1A shows various aspects of the prosthesis supplied with a penile opening on side in accordance with one embodiment.

Reference Numerals
- 10 cone
- 11 shaft
- 12 penile opening
- 13 material
- 14 prosthesis
- 15 penis
- 16 attaching method
- 17 prosthesis
- 18 attaching method
- 19 penis

DETAILED DESCRIPTION

FIG. 1A First Embodiment

One embodiment is illustrated in FIG. 1A (Bottom View). The prosthesis, having a length D1, is constructed of a completely rigid construction (13) to allow the prosthesis to be rigid enough for intercourse but of materials light enough to be practical but strong flexible enough for rapid use during intercourse. To allow the prosthesis to be inserted into the partner (10) the Cone is rounded at an end with that allows the insertion without discomfort. The cone herein described is not necessarily of a cone shape but may be of a shape that is of a design that is easily inserted into the partner. To allow sexual intercourse the shaft is constructed of a hollow elongate tubular design similar to the design of the penis and of rigid construction (11) to allow the erection simulation for the non erect or semi-erect penis, to be inserted into the partner. The prosthesis is designed with a penile slot opening, having a length D4 and width D3, to extend as needed from a circular open end, having diameter D2, shaft from the base of the prosthesis to (12) to allow the prosthesis to be mounted onto the penis through the slot. As the end of the prosthesis is open it is designed for the penis to extend through the open end to accommodate the wide variety and sizes of penises. This design allows for the act of intercourse to be preformed and the male to have full sensation. This is possible because the penis and the gland behind the head of the penis (which is where the sensation is felt) are fully exposed during intercourse via the slot opening. It also allows the sensation of intercourse to be felt on the full length of the base of the penis. With an approximately one inch wide adhesive tape, it can be secured to the back of the prosthesis and around the penis closest to the body to allow for a safe, comfortable, and pleasurable experience. The tape allows, for the wrapping and securing and removal of the prosthesis from the penis without the pain associated with the removal of tape from skin. This is due to the tape not having adhesive that wraps around the penis and scrotum but does have adhesive that attaches to the prosthesis. Any adhesive tape is acceptable though.

Figure 2A:
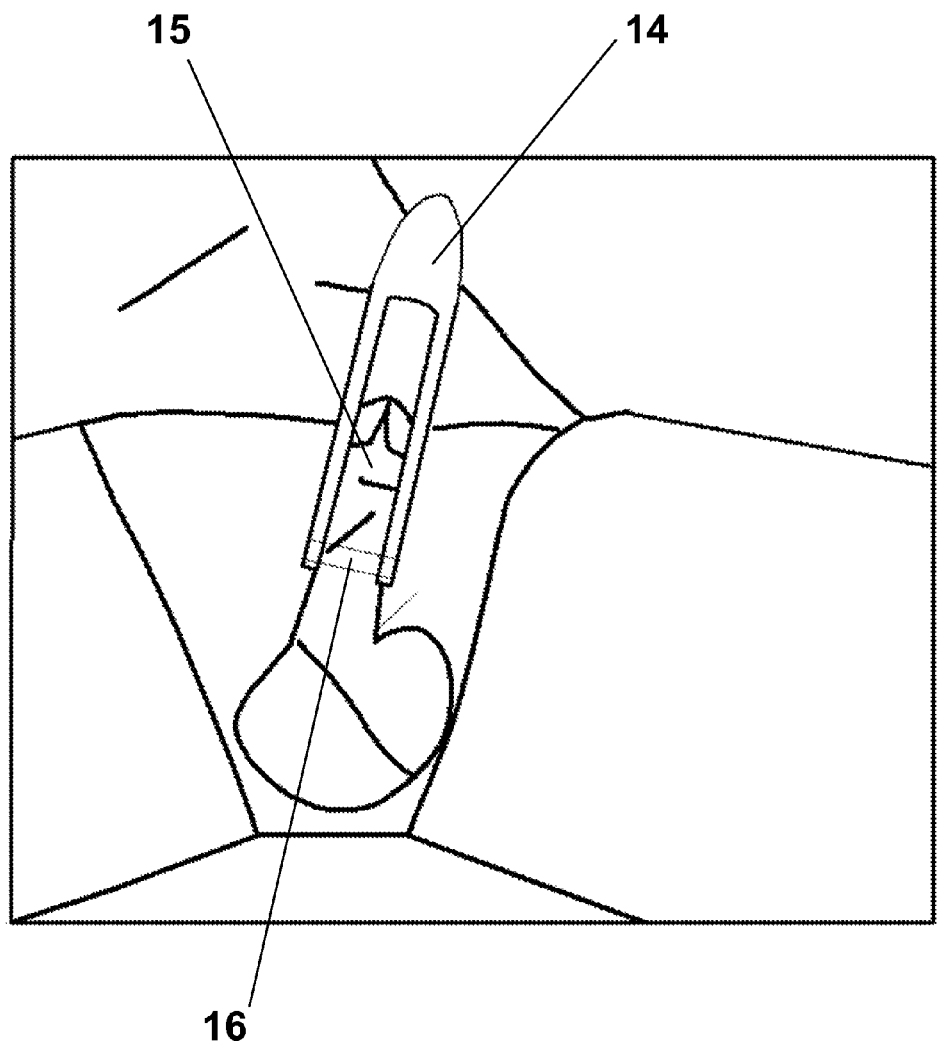
FIG. 2A shows the prosthesis mounted on the penis ready for use.

FIG. 2A Second Embodiment

Another embodiment is illustrated in FIG. 2A. This view shows the penis mounted into the prosthesis (14). As seen by this view the penis (15) is firmly mounted with the full length of the base of the penis is exposed for the full sensation during intercourse. (16) Shows the attaching method that is made up of a special adhesive tape that is wrapped around the base of the prosthesis and the penis. The tape is approximately one inch wide and has adhesive on approximately one inch at each end. The rest of the tape is non adhesive or very light adhesive so as not to stick to the flesh of the penis as it is removed. Any adhesive tape is acceptable though.

Figure 3A:
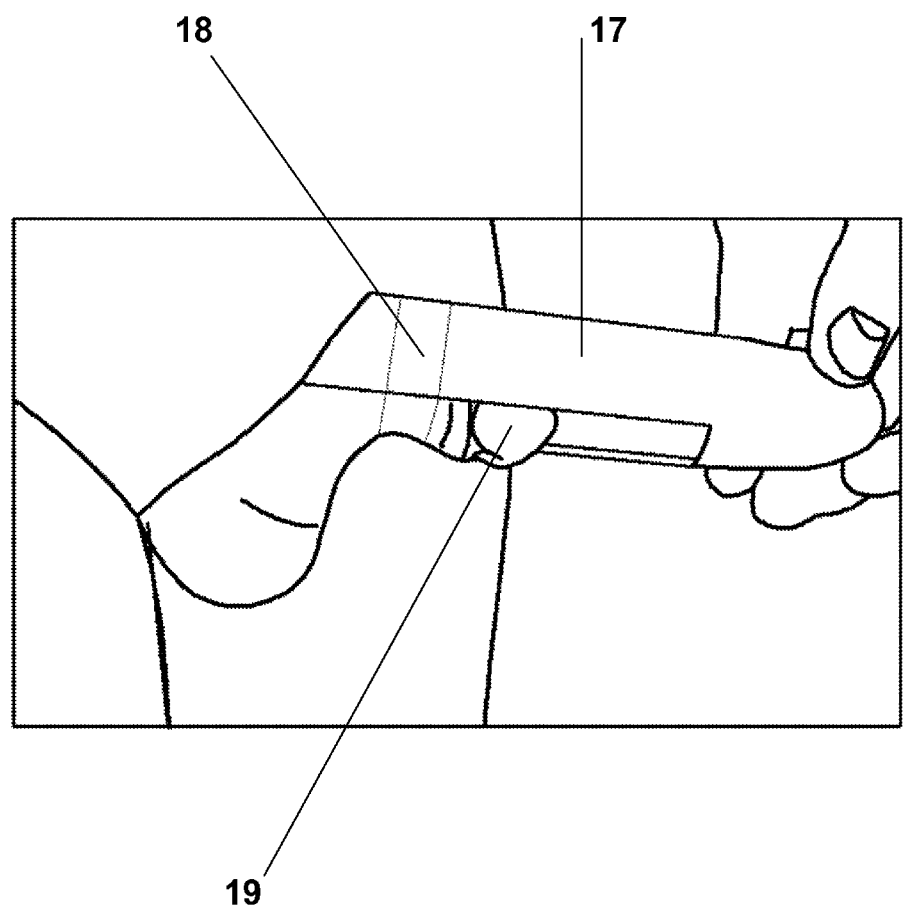
FIG. 3A shows the prosthesis installed as a side view ready for use.

FIG. 3A—Third Embodiment

Another embodiment is illustrated in FIG. 3A. This view shows the prosthesis as it mounted onto the penis from the side. As you look at the (17) prosthesis from the side the penis (19) is fully exposed for the act of intercourse with enough room for different sized penises. This allows room for different sized penises of men who may have a partially erect or fully impotent penis. When the special adhesive tape (18) is applied, the penis is fully attached and will not have the prosthesis fall off or the penis fall out of the penile slot during intercourse. The special design of the special medical cloth tape will not painfully stick to the penis when removed. Ay adhesive tape is acceptable though.

Operation—FIG. 1A, FIG. 2A, FIG. 3A

The manner of using the erection simulator prosthesis to perform sexual intercourse for a man with full or partial impotence (the inability to achieve a full or partial physical penile erection) is identical for a man who can achieve a physical penile erection. The man will grab hold of his penis and pull it to extend it as far as possible from his body. This is the same method for a male that is uncircumcised. For the uncircumcised male he will pull the penis to extend it as far as possible rolling the foreskin back to expose his penile gland. Then he will insert his penis into the penile slot of the prosthesis and the opening on the open end of the prosthesis. The slot side of the prosthesis should face down to expose the bottom side of his penis with the gland (which is the sensitive area of the penis). With the penis in position, and extended as far as possible, a strip of the special adhesive tape should be wrapped around the base of the penis and the base of the prosthesis to secure the penis in position. At this point, with the penis in place and secure, the man can perform sexual intercourse by inserting the cone end into the orifice of the partner. The special tap is designed to allow removal without the painful removal normal tape causes. Any adhesive tape is acceptable though.

CONCLUSIONS, RAMIFICATIONS, AND SCOPE

Accordingly the reader will see that the erection simulator prosthesis of the various embodiments can be used for a man who suffers from impotence. Even with a non erect penis, the man will be able to conveniently perform sexual intercourse, and the prosthesis can be removed just as easily. Furthermore the erection simulator prosthesis has additional advantages as follows:

That it can be attached firmly to the penis without elaborate and expensive methods.

It can be cleaned and made sanitary to prevent a danger of disease or infection.

That it has no sharp edges to incur injury or discomfort.

It can be seen that the expense, when compared with chemical medications, is no risk to health when a man is healthy enough to have sexual intercourse.

With the expense of Viagra and other penile erection drugs, the price considerably less.

When used properly it can satisfy the desires of the male as well as his partner.

It can be made of different materials with a rigid construction.

It can be made either with thicker or thinner material and or a combination of materials to accomplish its purpose.

It can be either clear in color or of different colors

It can be made to have different shapes, (like the same shape as a real or simulated penis).

It is designed to mount to penises of different lengths.

It is designed to mount to penises of different widths.

It has the ability to mount to a penis that is partially erect of fully impotent.

It is designed for penises that are uncircumcised.

The special tape allows the removal of the prosthesis from the penis without the pain associated with tape being removed from sensitive skin and still holds the prosthesis in place during sexual intercourse.

Any adhesive tape is acceptable.

Although the description above contains many specificities, these should, not be construed as limiting the scope of the embodiment but as merely providing illustrations of some of the embodiments. For example, the prosthesis can have a different inside or outside diameter either smaller or larger. The shaft with the cone can be longer or shorter in length. The penile opening can be either longer or shorter accommodating for different size penises. The penile opening may be either wider or narrower to allow the insertion of the penis. The cone is not necessarily the design of a cone. It can be made to resemble the physical shape of a an actual erect penis or similar to but is not limited to different shapes. Its design will be made for easy insertion into the partner. The attaching method can change.

Thus the scope of the embodiments should be determined by the appended claims and their legal equivalents, rather than by the examples given.

I claim:

1. A prosthesis for a penis, comprising:
a rigid elongate hollow tubular body having an inner volume capable of accepting the penis, the prosthesis having a circular opening into the hollow tubular body at a first end of the tubular body and extending into a conical shaped second end, opposite the first end, the second end consisting of a rounded apex; and
a longitudinal open slot along the length of the tubular body traversing the first end and terminating at a point prior to traversing the second end, said longitudinal open slot having a width of at least half a diameter of the circular opening;
wherein the penis is inserted into the prosthesis either by the first end or the slot and positioned within the tubular body so the first opening is adjacent to a base of the penis, a head of the penis does not extend into the second end and a bottom portion of the head of the penis lies along the slot in order to expose the bottom portion to stimulus during intercourse with an orifice.

2. The prosthesis of claim 1, wherein the prosthesis is manufactured from rigid material of high density poly ethylene.

3. The prosthesis of claim 1, wherein the prosthesis is of a size to resemble a human penis in an engorged, erect state.

4. The prosthesis of claim 1, wherein the prosthesis includes tape comprising an adhesive portion for adhering to the prosthesis and a portion lacking adhesive for securing skin around a base of the penis and a base of a scrotum positioned just beneath the penis.

5. The prosthesis of claim 1, wherein the longitudinal slot is approximately ⅔ of a total length of the prosthesis.

6. A method for using a prosthesis on a penis to achieve intercourse, comprising the steps of:
(a) inserting the penis into a prosthesis having a circular opening into the hollow tubular body at a first end of the tubular body and extending into a conical shaped second end, opposite the first end, the second end consisting of a rounded apex;
(b) positioning a bottom surface of the penis adjacent to a longitudinal open slot along the length of the tubular body of the prosthesis, the slot traversing the first end and terminating at a point prior to traversing the second end, said longitudinal open slot having a width of at least half a diameter of circular opening; and
(c) adhering the prosthesis to a base of the penis with tape having an adhesive portion for adhering around the tubular body and a portion without adhesive adhering from the prosthesis around the base of the penis enabling maintaining the bottom surface of the penis adjacent to the slot during intercourse with an orifice.

\* \* \* \* \*